United States Patent
Jiang et al.

(10) Patent No.: US 7,368,006 B2
(45) Date of Patent: May 6, 2008

(54) DEAERATION APPARATUS FOR DEAERATING WATER USED DURING ULTRASONIC FOCUSING TUMOUR TREATMENT

(75) Inventors: Jiwei Jiang, Shanghai (CN); Jiaxian Dong, Shanghai (CN); Baili Jin, Shanghai (CN); Yisheng Chen, Shanghai (CN); Guanlong Li, Shanghai (CN)

(73) Assignee: Shanghai A&S Science Technology Development Co., Ltd., Shanghai (CN)

( * ) Notice: Subject to any disclaimer, the term of this patent is extended or adjusted under 35 U.S.C. 154(b) by 535 days.

(21) Appl. No.: 10/535,271

(22) PCT Filed: Sep. 1, 2003

(86) PCT No.: PCT/CN03/00731

§ 371 (c)(1),
(2), (4) Date: May 17, 2005

(87) PCT Pub. No.: WO2004/047924

PCT Pub. Date: Jun. 10, 2004

(65) Prior Publication Data

US 2006/0064075 A1    Mar. 23, 2006

(30) Foreign Application Priority Data

Nov. 25, 2002   (CN) .......................... 02 2 79850 U

(51) Int. Cl.
*B01D 19/00* (2006.01)

(52) U.S. Cl. ............................ 96/157; 96/200; 95/249; 95/260

(58) Field of Classification Search ................... 96/200, 96/157, 173, 174; 95/260, 249, 248
See application file for complete search history.

(56) References Cited

U.S. PATENT DOCUMENTS

| | | | |
|---|---|---|---|
| 4,316,725 A * | 2/1982 | Hovind et al. ................. 95/248 |
| 4,816,044 A * | 3/1989 | Weisert et al. ................ 96/157 |
| 6,685,639 B1 * | 2/2004 | Wang et al. ................. 600/439 |

FOREIGN PATENT DOCUMENTS

| | | | |
|---|---|---|---|
| DE | 4034412 A1 * | 4/1992 |
| JP | 62217156 A * | 9/1987 |
| JP | 2104345 * | 4/1990 |

* cited by examiner

*Primary Examiner*—Duane Smith
*Assistant Examiner*—Douglas J. Theisen
(74) *Attorney, Agent, or Firm*—Rabin & Berdo, P.C.

(57) ABSTRACT

The present invention relates to a deaeration device for deaerating water used during ultrasonic focusing tumour treatment. The said deaeration device includes water purifiers (2), a vacuum pump (32), a water heater (6), electromagnetic valves (3, 5, 7-9, 19-23, 25-26, 30-31), water tanks (10, 18), content gauges (11, 15, 17), a thermometer (13), vacuum gauges (12, 16), and an aqueous capsule (24). The said vacuum pump (32) is a water jet vacuum pump, and there are two water tanks (10, 18). The vacuum pump (32) is connected to the tops of two water tanks (10,18) via a valve assembly composed of four electromagnetic valves (19-22). Two atomizing nozzles (14) are respectively provided at the water inlets on the tops of two water tanks (10,18).

2 Claims, 2 Drawing Sheets

DEAERATION APPARATUS FOR DEAERATING WATER USED DURING ULTRASONIC FOCUSING TUMOUR TREATMENT

TECHNICAL FIELD

The present invention relates to a deaeration device for deaerating water used during ultrasonic focusing tumour ablation treatment, which belongs to the field of medical equipments.

BACKGROUND ART

The purpose of water processing for water used during ultrasonic focusing tumour ablation treatment is to deaerate said water, i.e. to extract air solved therein out of said water, currently by means of water circulation vacuum deaeration, in which said water is circulated in a vacuum environment and the air solved in the water is separated out or deaerated thereby. Presently, the vacuum pumping unit in a water processing system for water used during ultrasonic focusing tumour ablation treatment uses a slide valve pump-Roots vacuum pump set or a water cycling vacuum pump-Roots vacuum pump set. The water circulation is made running by the water pump, since the slide valve pump is a kind of oil-seal vacuum pump and water is processed therein, the water undergoes vapourization and condensation, thus often there is water coming into the slide valve pump, causing contamination to the oil. The water cycling pump makes quite strong noise, and these two kinds of pumps have complicated structures and high costs. The water circulation in those water processing systems relies on their water pumps, which operate at very low efficiencies under vacuum environment, and of which the water outlet has to be put below water level otherwise the water will not come out. Even if the water outlet is put below water, the water pump can operate only when the water has been deaerated to some extent. And the water pump cannot maintain normal operation during the whole deaerating process, and putting the water outlet within the water does no good to the deaeration. Furthermore, the deaeration is not very effective by the single time deaerating using just a single water tank.

PURPOSE OF THE INVENTION

To overcome said shortcomings of the prior art, the present invention provides a deaeration device for deaerating water used during ultrasonic focusing tumour ablation treatment, which applies a water jet vacuum pump and utilizes alternating vacuum suctions of twin water tanks, and in which the water circulation is caused by the atmospheric pressure and atomizing nozzle is utilized for spraying the water at the outlet thereof.

SUMMARY OF THE INVENTION

The technical solution for the deaeration device of the present invention is described as the following, wherein a tap water main inlet is connected to a water purifier and a vacuum pump separately, the common pipe for the cold and heated water from the water purifier and a water heater is connected to a water tank via a electromagnetic valve, the vacuum pump is connected to the top of the water tank via electromagnetic valves and a vacuum switching valve, there are content gauges, a thermometer and vacuum gauges set on the water tank, and the bottom of the water tank is connected to an aqueous capsule via electromagnetic valves and a water pump, this deaeration device is characterized as: said vacuum pump is a water jet vacuum pump; said water tank is comprised of twin tanks: water tank A and water tank B, and a water cycling mechanism with twin-tank alternating vacuum suctions is formed by said water jet vacuum pump in connection with said water tank A and water tank B at their tops via a valve assembly composed of four electromagnetic valves; and two atomizing nozzles are provided at the water inlets respectively on the tops of said two water tanks.

In comparison with a slide valve pump, the water jet vacuum pump utilized in the present invention has the advantages of simple structure, reliable operation, low noise, no contamination, and long lifetime. In the water cycling mechanism with twin-tank alternating vacuum suctions, the water circulation is pushed by atmospheric pressure with alternating vacuum suctions of said twin tanks, no mechanical pumping is needed here, thus its operation is simple and reliable, and the water route and air route are both controlled with electromagnetic valves, which is accessible by automation. Instead of being put below water, both water inlets are set respectively at the tops of the twin water tanks in the form of atomizing nozzles, thus the water coming out is atomized and sprayed out immediately as tiny foggy droplets into vacuum environments in each of the tanks, i.e. the area for the water to contact the vacuum environment is increased enormously in these droplets, and the deaerating is largely promoted during the fast movement of those foggy droplets. Furthermore, water in the lower parts of the tanks is scoured and stirred by these foggy droplets in high speed, facilitating a second time deaeration of these water in the lower parts of the water tanks.

DETAILED DESCRIPTION OF THE PREFERRED EMBODIMENT

Figure 1:
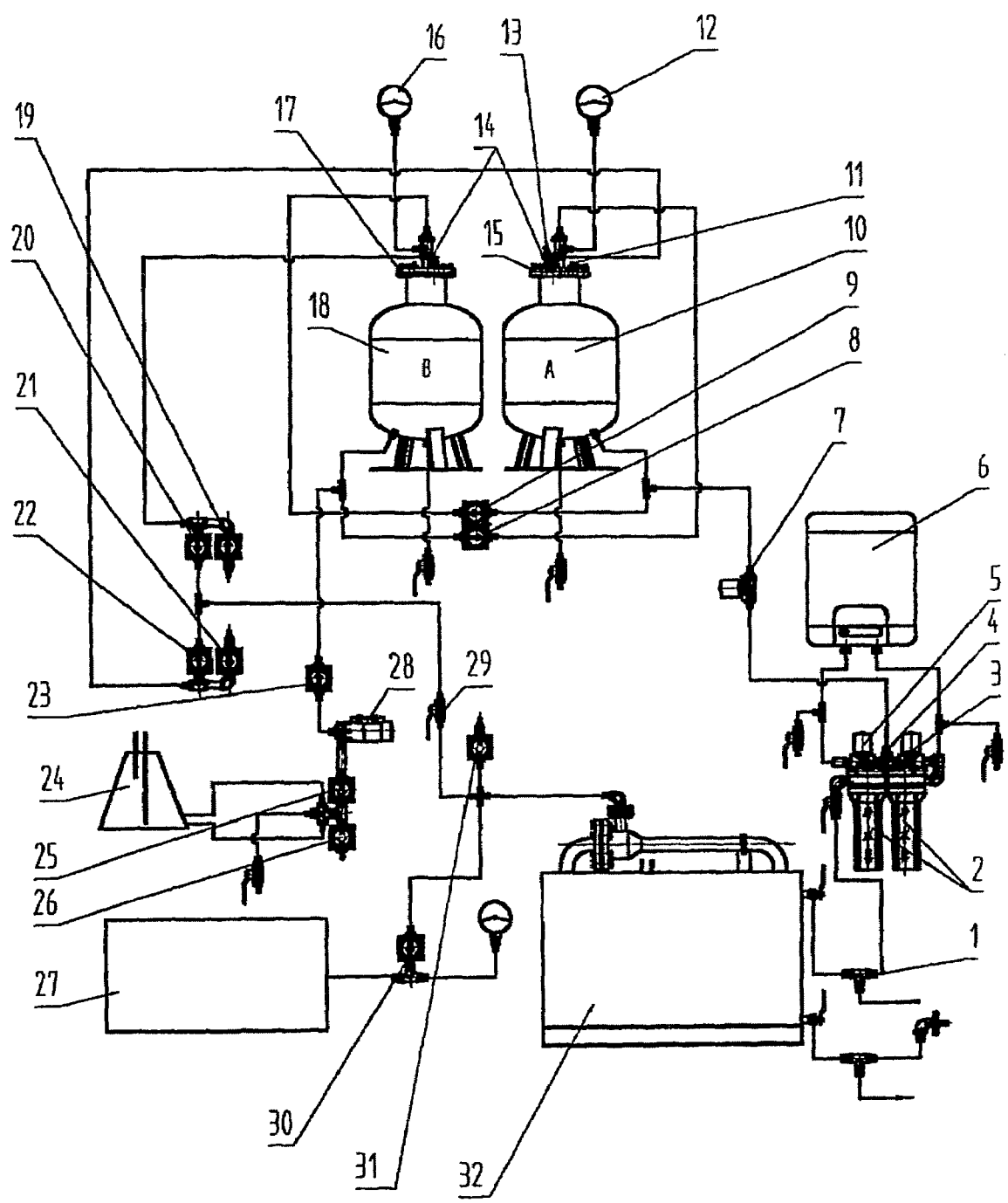
FIG. 1 is a scheme diagram of the principle of the deaeration device for deaerating water used during ultrasonic focusing tumor ablation treatment according to the present invention.
Figure 2:
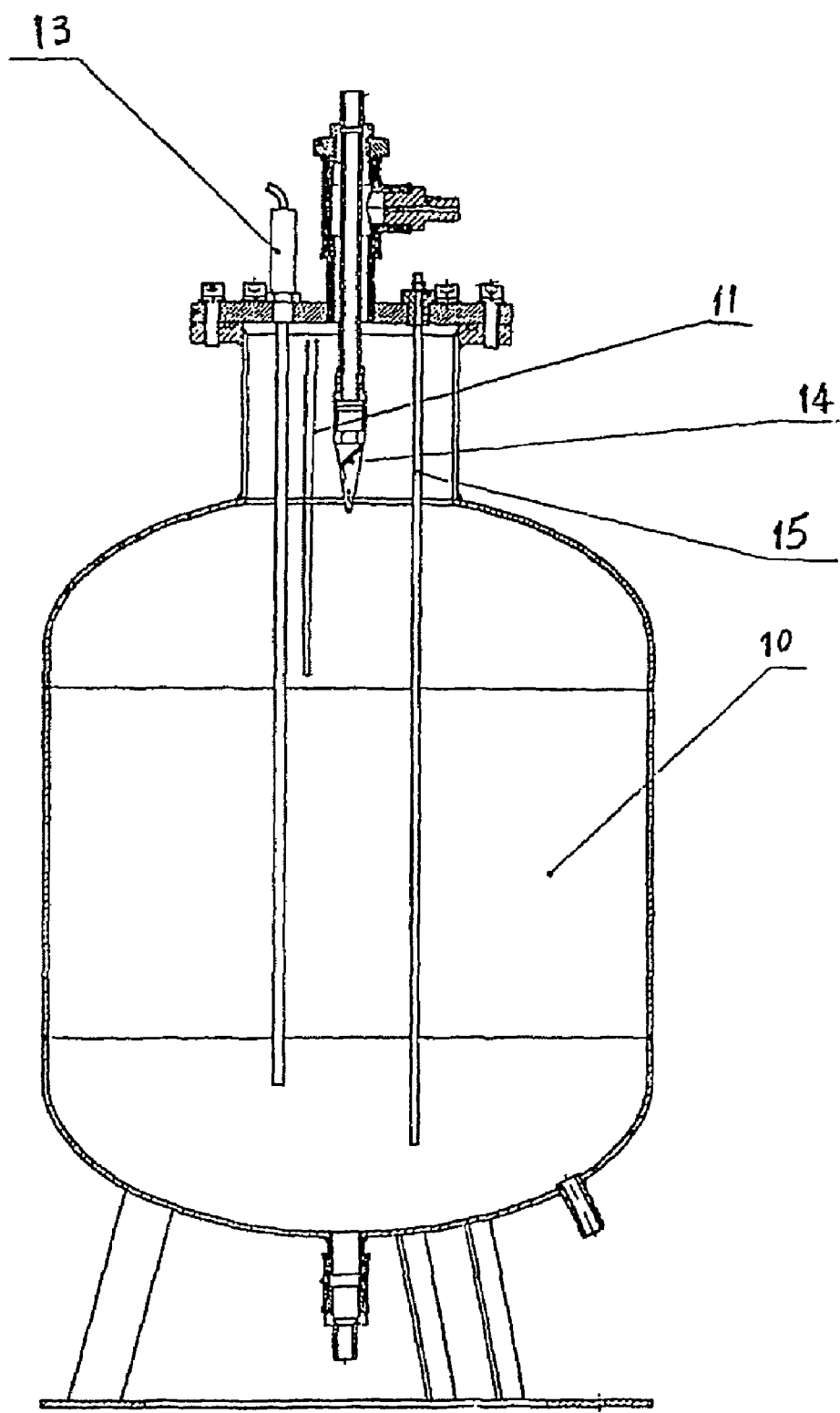
FIG. 2 is a scheme diagram of the structure of the water tank A.

Referring to FIGS. 1 and 2 showing the deaeration device of the present invention, tap water main inlet 1 is connected to water purifiers 2 and a vacuum pump 32 separately, the common pipe 4 for the cold and heated water from the water purifiers 2 and a water heater 6 is connected to a water tank A 10 via a electromagnetic valve 7, the inlet of the vacuum pump 32 is connected to the tops of two water tanks A 10 and B 18 via a vacuum switching valve 29 and electromagnetic valves 20 and 22, there are content gauges 11, 15, and 17, a thermometer 13, and vacuum gauges 12 and 16 set separately on the tops of both water tanks, and the bottom of the water tank B 18 is connected to an aqueous capsule 24 via a electromagnetic valve 23, a water pump 28, and a electromagnetic valve 25, said deaeration device is characterized in that said vacuum pump 32 is a water jet vacuum pump; said water tanks are comprised of twin tanks: water tank A 10 and water tank B 18, and a water cycling mechanism with twin tank alternating vacuum suctions is formed by said water jet vacuum pump in connection with said water tank A 10 and water tank B 18 at their tops via a valve assembly composed of four constant-open electromagnetic valves 19, 20, 21, and 22; and two atomizing nozzles 14 are provided at the water inlets on the tops of water tank A 10 and water tank B 18, respectively.

The operation of said deaeration device can be described as follows: referring to FIG. 1, incoming water through the tap water main inlet 1 is divided into two routes, one route goes to the vacuum pump 32 as its operation water, the other is directed to the water purifiers 2 to be filtered therein and then to the water heater 6, and it depends on the temperature inside water tank A 10 as measured by thermometer 13 set on the top of tank A 10 whether to input cold water or hot water into water tank A 10, cold purified water from said purifier 2 will be sent directly into water tank A 10 via electromagnetic valve 7 when said temperature is high and the electromagnetic valve 3 is open, otherwise hot water will be sent into water tank A 10 via electromagnetic valve 7 when said temperature is low and the electromagnetic valve 5 is open. When the water level in tank A 10 as measured by the content gauge 11 reaches a predetermined height, valve 7 is closed, and constant-open electromagnetic valves 19 and 22 are closed, vacuum pump 32 is started to pump air out of water tank B 18 with vacuum gauge 16 detecting the vacuum inside tank B 18, when said vacuum inside tank B reaches a predetermined value, valve 9 is open, the water inside tank A 10 goes from its bottom via valve 9 entering the top of tank B 18 through nozzle 14 and being atomized and sprayed out, these atomized water droplets are deaerated under the vacuum environment of tank B 18, and such deaerated water is accumulated in tank B 18 with water level in tank A 10 decreasing until reaching a predetermined low level, then content gauge 15 signals, valve 9 is closed and after pumping tank B 18 continues for about 30 seconds, electromagnetic valves 20 and 21 are closed and electromagnetic valves 19 and 22 are opened, then the vacuum in water tank B 18 is broken and the air in water tank A 10 is pumped out until the vacuum inside tank A 10 as detected by vacuum gauge 12 reaches a predetermined value, valve 8 opens, the first-time deaerated water in tank B 18 goes from its bottom via valve 8 entering the top inlet of tank A 10 through nozzle 14 and being atomized and sprayed out into tank A 10, these atomized water droplets are deaerated a second time under the vacuum environment of tank A 10, and the water level in tank B 18 as measured by content gauge 17 decreases until reaching a predetermined low level, then valve 8 is closed and after about 30 seconds, electromagnetic valves 19 and 22 are closed and electromagnetic valves 20 and 21 are opened, the vacuum in tank A 10 is broken, and air inside water tank B 18 is again pumped out with its vacuum being detected by vacuum gauge 16 until all the water returns back to tank B 18, then the cycle is jumped out with vacuum pump 32 closed, and electromagnetic valves 23 and 25 open, the water pump 28 is started to inject said cycling-deaerated water from tank B 18 into aqueous capsule 24 for the use in the ultrasonic focusing tumour ablation treatment. And a cushion 27 for fixing the patient's body is then vacuumized by vacuum pump 32 in coordination with vacuum switching valve 29 and electromagnetic valves 30 and 31.

The invention claimed is:

1. A deaeration device for deaerating water used during ultrasonic focusing tumour ablation treatment, wherein a tap water main inlet is connected to a water purifier and a vacuum pump separately, a common pipe for cold and heated water from the water purifier and a water heater is connected to a water tank via electromagnetic valves, the vacuum pump is connected to the top of the water tank via electromagnetic valves and a vacuum switching valve, there are content gauges, a thermometer, and vacuum gauges set on the water tank, and the bottom of the water tank is connected to an aqueous capsule via electromagnetic valves and a water pump, said deaeration device is characterized in that said vacuum pump is a water jet vacuum pump (32);

said water tank is comprised of twin tanks: water tank A (10) and water tank B (18), and a water cycling mechanism with twin-tank alternating vacuum suctions is formed by said water jet vacuum pump (32) in connection with said water tank A (10) and water tank B (18) at their tops via a valve assembly composed of four constant-open electromagnetic valves (19, 20, 21, 22); and two atomizing nozzles (14) are provided at the respective water inlets on the tops of said water tank A (10) and water tank B (18).

2. The deaeration device for deaerating water used during ultrasonic focusing tumour ablation treatment according to claim 1, characterized in that a high-level content gauge (11), a low-level content gauge (15), a thermometer (13), and a vacuum gauge (12) being mounted on the top of said water tank A (10), and a content gauge (17) and a vacuum gauge (16) being mounted on the top of said water tank B (18).

* * * * *